United States Patent
Wang

(10) Patent No.: US 10,646,143 B2
(45) Date of Patent: May 12, 2020

(54) OPTICALLY DISCRIMINATIVE DETECTION OF MATTERS IN TISSUES AND TURBID MEDIA AND APPLICATIONS FOR NON-INVASIVE ASSAY

(71) Applicant: Alethus, Inc., Medford, MA (US)

(72) Inventor: Feiling Wang, Medford, MA (US)

(73) Assignee: Alethus, Inc., Medford, MA (US)

( * ) Notice: Subject to any disclaimer, the term of this patent is extended or adjusted under 35 U.S.C. 154(b) by 1042 days.

(21) Appl. No.: 14/773,755

(22) PCT Filed: Mar. 8, 2013

(86) PCT No.: PCT/US2013/029980
§ 371 (c)(1),
(2) Date: Sep. 8, 2015

(87) PCT Pub. No.: WO2014/137357
PCT Pub. Date: Sep. 12, 2014

(65) Prior Publication Data
US 2016/0022178 A1    Jan. 28, 2016

(51) Int. Cl.
*A61B 5/1455* (2006.01)
*A61B 5/145* (2006.01)
*A61B 5/00* (2006.01)

(52) U.S. Cl.
CPC .......... *A61B 5/1455* (2013.01); *A61B 5/0059* (2013.01); *A61B 5/14532* (2013.01); *A61B 5/443* (2013.01); *A61B 5/6826* (2013.01); *A61B 5/6887* (2013.01); *A61B 5/7257* (2013.01); *A61B 5/7278* (2013.01); *A61B 2560/0406* (2013.01)

(58) Field of Classification Search
None
See application file for complete search history.

(56) References Cited

U.S. PATENT DOCUMENTS

| 5,882,301 A * | 3/1999 | Yoshida | A61B 5/1455 600/318 |
| 6,223,063 B1 * | 4/2001 | Chaiken | A61B 5/02427 600/310 |
| 8,581,697 B2 * | 11/2013 | Ridder | A61B 5/0059 340/5.82 |
| 2002/0115918 A1 | 8/2002 | Crowley | |
| 2010/0252721 A1 | 10/2010 | Xu | |
| 2011/0245686 A1 | 10/2011 | Wang | |

FOREIGN PATENT DOCUMENTS

| WO | 1993007801 A1 | 4/1993 |
| WO | 2011091804 A1 | 8/2011 |

* cited by examiner

*Primary Examiner* — Eric F Winakur
*Assistant Examiner* — Marjan Fardanesh
(74) *Attorney, Agent, or Firm* — Perkins Coie LLP

(57) ABSTRACT

Non-invasive optical detection devices and techniques that use optically discriminative detection of returned probe light from a target by spatially separating the returned probe light from the deep tissue structure and the returned probe light from the skin surface and the shallow tissue structure based on different wave vector components to improve the optical detection sensitivity in detecting the returned probe light from the deep tissue structure with reduced optical interference by the returned probe light form the skin surface and the shallow tissue structure.

21 Claims, 14 Drawing Sheets

OPTICALLY DISCRIMINATIVE DETECTION OF MATTERS IN TISSUES AND TURBID MEDIA AND APPLICATIONS FOR NON-INVASIVE ASSAY

CROSS REFERENCE TO RELATED APPLICATION

This patent document is a 35 U.S.C. § 371 National Stage application of PCT Application No. PCT/KR2013/029980, filed on Mar. 8, 2013. The entire disclosure of the above application is incorporated by reference in its entirety as part of this document.

TECHNICAL FIELD

This patent document relates to devices and methods for optically characterization and measurements of tissues and other turbid media, including applications in non-invasive measurements of glucose levels.

BACKGROUND

Non-invasive or in vivo interrogation of biological tissues with light waves is becoming increasingly important in medicine. Some of the techniques employed are diffuse-reflectance spectroscopy, fluorescence measurement, imaging etc. In various applications for taking measurements from biological tissues, the targeted tissues tend to be under the skin as subsurface tissues such as the fluorescence-based detection of cancerous tissues. Specifically, testing glucose levels based on blood tests requires measurements of blood samples by first obtaining blood samples and then conducting measurements of obtained the blood samples. Many conventional glucose testing techniques based on measuring blood samples use a lancing device to actuate a lancet to cut a target skin location such as a patient's fingertip to obtain a small amount of blood for blood testing and to measure the blood glucose level. This and other blood testing methods require cutting of the skin and thus are invasive.

SUMMARY

This patent document includes non-invasive optical detection devices and techniques that use optically discriminative detection of returned probe light form a target by spatially separating the returned probe light from the deep tissue structure and the returned probe light from the skin surface and the shallow tissue structure based on different wave vector components to improve the optical detection sensitivity in detecting the returned probe light from the deep tissue structure with reduced optical interference by the returned probe light form the skin surface and the shallow tissue structure.

In one implementation, a non-invasive optical device is provided for optically characterizing a target tissue under the skin and includes a device housing that forms an enclosure and an optical window in the enclosure that transmits light and provides a surface for a person to place a finger or body part thereon; a light source located inside the device housing to produce probe light that transmits through the optical window to reach the finger or body part and to produce returned probe light from the finger or body part which carries information of an illuminated part of the finger or the body part for optically characterizing a target tissue inside the finger or body part; a lens located inside the device housing in an optical path of the returned probe light to perform a Fourier transform on different portions of the returned probe light of different optical wave vectors to direct the different portions of the returned probe light onto different locations on or near a focal plane of the lens; an optical detector module located inside the device housing and positioned at or near the focal plane of the lens and configured to include one or more optical detectors to spatially selective one or more selected portions of the returned probe light from the different portions of the returned probe light for detecting the target issue while spatially rejecting, from the one or more optical detectors, other portions of the different portions of the returned probe light that represent majority of the probe light returned by the skin surface and tissue layers above the target tissue; and a processing unit that receives output of the optical detector and processes the received output to extract information of the target tissue.

In another implementation, a device is provided for optically characterizing tissues or turbid media and includes a light source; means for directing a beam of light from the light source to a target area inside a tissue or turbid medium; a lens placed in the path of the backscattered light from the tissue or turbid medium; a photodetector having electrically isolated photo-sensing surfaces shaped to collect near-axis light and off-axis light separately; and a processing unit that receives output of the photodetector and processes outputs from the off-axis light to extract information of the target area inside the tissue or turbid medium.

In another implementation, a device is provided for optically characterizing tissues or turbid media and includes a light source that emits probe light; an optical fiber having a first fiber terminal coupled to receive the probe light from the light source and a second fiber terminal to output the probe light from the light source; a ring-shaped photodetector that includes a center opening to allow insertion of the second fiber terminal of the optical fiber; and a lens positioned to project a beam of concentrated light onto a tissue or turbid medium and to receive backscattered light from the tissue or turbid medium. The lens is located between the ring-shaped photodetector and the tissue or turbid medium to be away from the ring-shaped photodetector by a spacing equal to or near a focal length of the lens to direct off-axis portions of the backscattered light to the ring-shaped photodetector while directing on-axis or near-axis portions of the backscattered light into the second fiber terminal. This device also includes a processing unit that receives output of the ring-shaped photodetector and processes the output to extract information of a target inside the tissue or turbid medium.

In another implementation, a device is provided for optically characterizing tissues or turbid media and includes a light source to produce probe light; means for directing the probe light to a tissue or turbid medium; a lens in a path of backscattered probe light from the tissue or turbid medium; a beam stop having an opaque area located a focal length away from the lens; a photodetector having a photo-sensing area larger than the beam stop, located behind the beam stop to receive the backscattered probe light from the tissue or turbid medium that is not blocked by the beam stop; and a processing unit that receives output of the photodetector and processes the output to extract information of a target inside the tissue or turbid medium.

In yet another implementation, a device is provided for optically characterizing tissues or turbid media and includes a plurality of light sources emitting probe light at different wavelengths; means for directing of the probe light from each light source to a tissue or turbid medium; a lens placed in a path of backscattered light from the tissue or turbid medium; a beam stop having an opaque area and positioned at a distance of a focal length behind the lens to block light that is on or near an axis of the lens; means for receiving output light from the lens and the beam stop and for separating the output light into different light signals at the different wavelengths; a plurality of photodetectors located to receive the different light signals at the different wavelengths, respectively; and a processing unit that receives outputs of the photodetectors and processes the outputs to extract information of a target inside the tissue or turbid medium.

These and other implementations of the disclosed devices and methods are described in greater detail in the description, the drawings and the claims.

DETAILED DESCRIPTION

Figure 1:
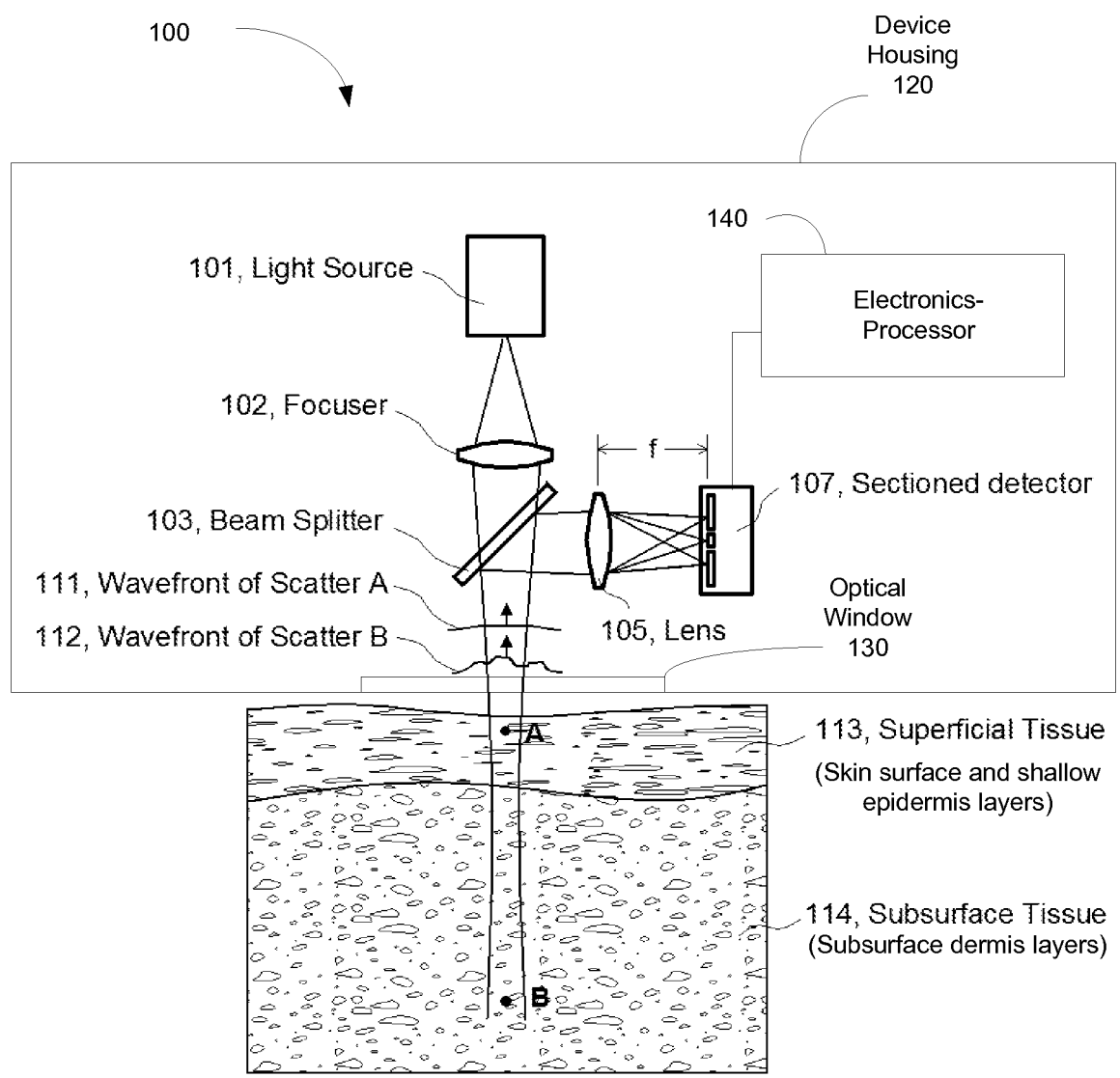
FIGS. 1 and 2 show an example of an non-invasive optical detection device based on optically discriminative detection and its operation.

Body tissues and various turbid media are types of media in which light experiences absorption, reflections or scattering. For assays and related processes, probe light can be sent into tissues of interest and the backscattered or reflected probe light or the fluorescent light at a different wavelength from the probe light can be collected for analyses. The collected light includes contributions from the specular reflection of the surface and backscattered light or fluorescent light from a range of depths with the tissues. Optically speaking, there is a significant difference between light radiated by the superficial layers (including the surface reflection) and light radiated by the subsurface volumes in turbid media. The latter carries much stronger wavefront distortions as such light must travel a greater distance in the tissues or turbid media before reaching the collection optics.

Optical detection based on optical reflection or back scattering of probe light directed to a tissue can be used to, in principle, provide non-invasive diagnostic measurements of tissues where the probe light is used to illuminate and probe the tissue without any cutting.

In various measurements or diagnostic tests, the targeted issue of interest may be located in the subsurface dermis structure where blood vessels or glucose-retaining vasculature and interstitial fluids reside. When the probe light is intended to reach such a target tissue in the subsurface dermis structure, the probe light must first penetrate through the top skin surface and the shallow epidermis layers of the skin and is attenuated due to optical absorption, reflection and scattering in its path of reaching the subsurface dermis structure. Additional attenuation caused by the absorption, reflection or scattering occurs to the returned probe light from the subsurface dermis structure. As a result, the final emerged returned probe light from the subsurface dermis structure is relatively weak relative to the light reflected from or scattered by the skin surface and shallow epidermis layers of the skin. Therefore, the light reflected from or scattered by the deeper subsurface dermis structure can be overwhelmed by or completely buried by the much stronger probe light reflected from or scattered by the skin surface and shallow epidermis layers of the skin. This interference by the strong light reflected from or scattered by the skin surface and the shallow epidermis layers of the skin presents a technical difficulty in achieving sensitive and accurate optical detection when the target tissue is located in the dermis structure or a deeper subsurface structure.

The devices and techniques disclosed in this patent document are in part based on recognition that the optical wavefront of light coming from a deeper tissue structure is perturbed or distorted more significantly than the optical wavefront of light coming from the skin surface and a shallower tissue structure. Therefore, when the initial probe light directed to a tissue has a well-defined wavefront (e.g., a Gussian beam with a smooth wavefront), the returned probe light from a shallower tissue structure experiences less perturbation by various structures along its optical path than the returned probe light from a deeper tissue structure. As a result, the wavefront of the returned probe light from the skin surface and shallower tissue structure, although showing wavefront distortions, is closer to the initial wavefront than the wavefront of the probe light from the shallow tissue structure. In the wave vector space, the wavefront of the returned probe light from the skin surface and shallow tissue structure has mostly wave vector components that are either equal to or closer to the wave vector or wave vectors of the initial wavefront while having some wave vectors caused by the perturbations and distortions that significantly deviate from the wave vector or wave vectors of the initial wavefront. In contrast, the wavefront of the returned probe light from the deep tissue structure has mostly wave vector components caused by the perturbations and distortions that significantly deviate from the wave vector or wave vectors of the initial wavefront while having some wave vector components that are either equal to or closer to the wave vector or wave vectors of the initial wavefront. This difference in the wave vectors between the returned probe light from the deep tissue structure and the returned probe light from the skin surface and the shallow tissue structure can be used to spatially separate the majority of the relatively weak returned probe light from the deep tissue structure and the majority of the relatively strong returned probe light from the skin surface and the shallow tissue structure. Accordingly, this optically discriminative detection can be used to provide sensitive detection of the relatively weak returned probe light from the deep tissue structure with significantly reduced interference from the majority of the relatively strong returned probe light from the skin surface and the shallow tissue structure.

Examples of implementing the devices and techniques based on optically discriminative detection disclosed in this patent document use a lens system with one or more lenses to process the total returned probe light from the target tissue and separates the returned probe light from the deep tissue structure and the returned probe light from the skin surface and the shallow tissue structure based on the above difference in their wave vector components via Fourier transform by the lens system. One or more optical detectors can be placed at certain spatial locations to capture the separated majority of the returned probe light from the deep tissue structure without receiving the majority of the returned probe light from the skin surface and the shallow tissue structure. The detector outputs of such one or more optical detectors can be processed to extract information carried by the returned probe light indicating properties of the deep tissue structure, e.g., the glucose level of the fluids in the deep tissue structure, e.g., glucose-retaining body fluids such as vasculature and interstitial fluids. In some implementations, the majority of the returned probe light from the skin surface and the shallow tissue structure that is separated by the lens system may be directed to a beam dump to avoid scattering of such light to cause optical interference affecting the above one or more optical detectors, or, alternatively, may be directed to one or more additional optical detectors at appropriate locations that are separated from the above one or more optical detectors. Therefore, the present devices and methods treat optical signals radiated from tissues and turbid media differentially based on their depth-dependent wavefront characteristics from the surface by using optically discriminative detection to facilitate better optical analysis of the substance of interest in the target media. Notably, the non-invasive optical devices and methods disclosed here can be adopted to apply to detection of objects beneath surfaces of various media or structures other than tissues and turbid media to reduce the undesired interference by light from the top surface and shallow structures above the targeted objects.

The disclosed devices and techniques for non-invasive optical characterization of tissues separate light radiated, reflected or scattered by subsurface volumes separately from light radiated, reflected or scattered by surface layers to enable improved detection of light radiated, reflected or scattered by subsurface volumes. The disclosed devices and techniques can benefit a variety of optical characterization procedures in which the targeted tissue or object is below the surface or subsurface, as in some applications of reflectance spectroscopy, fluorescence-based imaging as well as non-invasive monitoring of the glucose level in body fluids such as glucose-retaining vasculature and interstitial fluids.

FIG. 1 shows an example of a non-invasive optical test device 100 that implements the above optically discriminative detection with different photo-sensing elements based on lightwaves of different wavefront characteristics from different depths of a tissue. Such a testing device 100 includes a device housing 120 that forms an enclosure in which various components and electronics are located and an optical window 130 at a location of the device housing 120 that transmits light and provides a surface for a person to place a finger or a body part for performing a test such as a glucose test by detection of returned probe light from glucose-containing body fluids in the dermis structures. A light source 101 is provided inside the device housing 120 to produce probe light that transmits through the optical window 130 to reach the finger and to produce returned probe light from the finger which carries information of an illuminated part of the finger for performing the glucose test. A lens assembly 102 is provided to optically condition the probe light from the light source 101, e.g., collimating or focusing the probe light towards the optical window 130. The wavefront of the probe light output by the lens assembly 102 generally has a smooth wavefront. An optical beam splitter 103 is placed in an optical path of the probe light between the lens assembly 102 and the optical window 130 to direct returned probe light from the finger to a lens assembly 105 of a focal length f that spatially separates different portions of the returned probe light for the optically discriminative detection. A sectioned optical detector module 107 is provided located at or near the focal plane of the lens assembly 105 and includes different optical sensing elements or optical detectors at different locations that receive the output probe light from the lens assembly 105. A device control unit 140 is provided to include electronics and a processor and operates to provide user interface and control functions for the user to operate the device when performing the test and to provide a user display feature to output the test results and other user control functions. In some implementations, the device control unit 140 may include a display screen and physical user buttons for the user to operate the device, e.g., turning on or off the power of the device, activating the optical detection, or selecting control display modes of the test results and other device status information on the display screen. In other implementations, the device control unit 140 may include a touch screen that provides both the display window for displaying information and a touch interface for user control operations.

This arrangement in FIG. 1 can be used to separate light radiated by the superficial layers such as the skin surface and the epidermis layers 113 of a tissue from light radiated by subsurface volumes 114 such as the dermis layers. This is accomplished by the combined use of the lens 105 and the sectioned detector 107. For light signals with a smooth wavefront, the lens 105 operates to focus the light into a tight spot located on or near the optical axis of the lens 105 at or near the focal plane of the lens 105; for light signals with randomized wavefronts, the lens 105 operates to disperse the light energy in the lens focal plane. The sectioned detector 107 includes different optical sectioned sensing elements or detectors, e.g., a center element that picks up near-axis light (mainly from superficial tissue 113) while off-center optical sensing elements such as a ring-shaped peripheral optical sensing element that is isolated from the center element can pick up off-axis light (mainly originated from subsurface volumes 114). Specifically, FIG. 1 shows a structure A located in the near the skin surface in the shallow epidermis layers 113 which produces a portion 111 of the returned probe light and a structure B located in the deep subsurface dermis layers 114 which produces a portion 112 of the returned probe light.

In FIG. 1, the device control unit 140 processes the outputs from different sensing elements of the sectioned detector 107 to extract the information of a target tissue location (e.g., B in FIG. 1). As discussed above, the returned probe light 112 that is mainly caused by the scatter B in the dermis layers 114 is received by the off-center optical sensing elements of the sectioned detector 107 and provides the information on the scatter B. Various data extraction algorithms can be applied in the device control unit 140 in extracting the target information.

Figure 2:
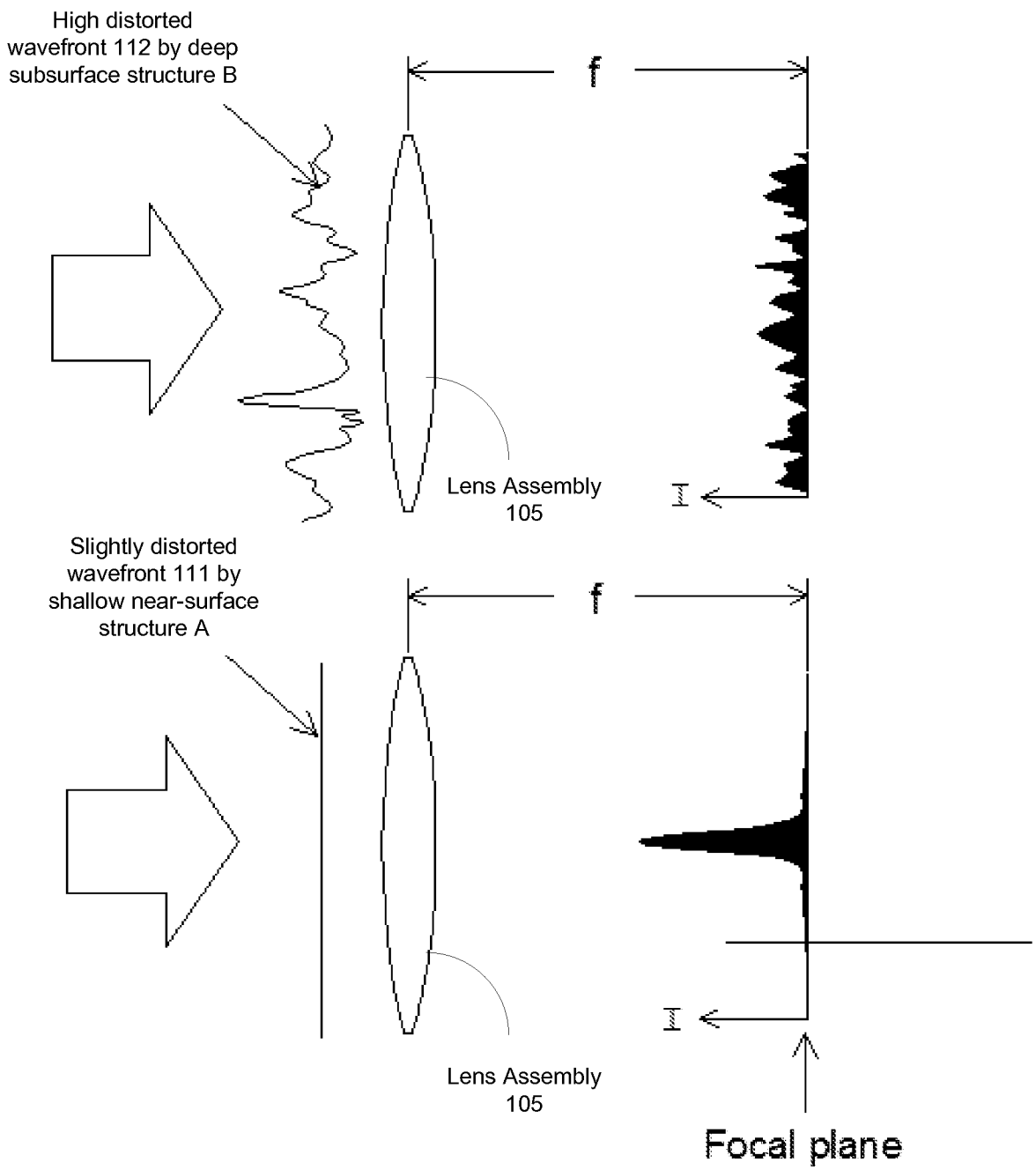

FIG. 2 illustrates behaviors of different optical wavefronts from different portions 111 and 112 of the returned probe light from the finger in operating the device in FIG. 1. The distribution of light intensity in the focal plane of the lens 105 is determined by the Fourier transform of the wavefront of each portion of the returned probe light from the finger. For light with no or little distortion such as the probe light portion 111 from the shallow near-surface structure A near the skin surface in the shallow epidermis layers 113, most of the optical energy tends to be converged to the center of the focal plane due to the lack of high-frequency spatial variation of the optical phase in the wavefront; if the wavefront of the incoming light is highly distorted or randomized such as the probe light portion 112 from the structure B located in the deep subsurface dermis layers 114 the optical energy tends to be dispersed in the focal plane as high-frequency spatial components predominate. The photo-sensing surface of the detector 107 can be located in the focal plane of the lens 105 to provide different sensing areas for detecting different spatial portions of the returned probe light that come back from different depths of the target tissue, respectively and one sensing area on the detector 107 is designated to detect one portion of the returned probe light mainly from a corresponding depth or region under the surface.

Figure 3:
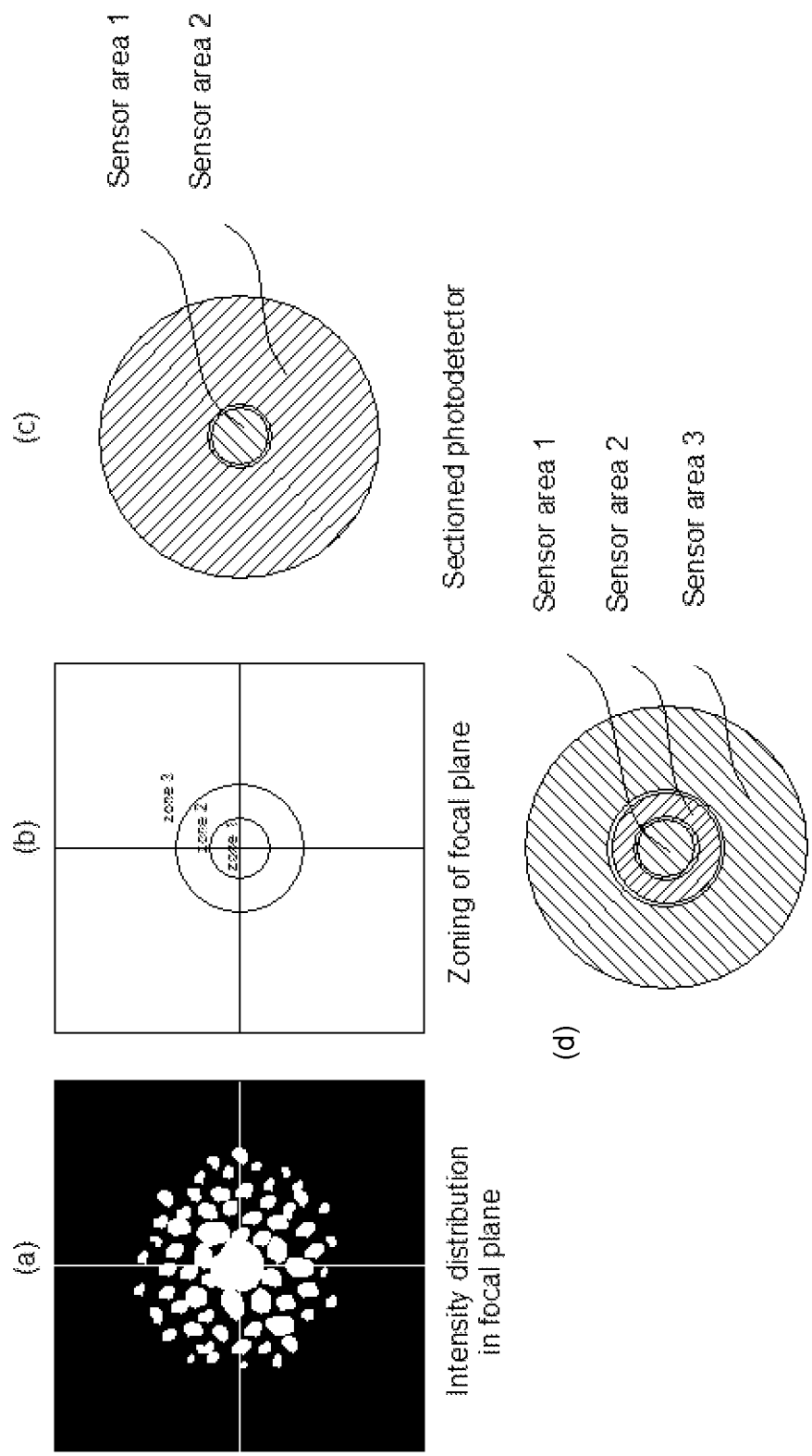
FIG. 3 shows examples of sectioned optical detectors for detecting different spatial portions of the returned probe light in FIG. 1 and other designs.

FIG. 3 shows an example of a sectioned optical detector with different and isolated concentric sensing zones. FIG. 3(a) shows the overall intensity spatial distribution of the entire returned probe light at the focal plane of the lens 105. FIG. 3(b) shows a zoning of the focal plane into 3 zones: central Zone 1, middle ring Zone 2 and outer ring Zone 3. A portion of the returned probe light with a smooth wavefront (plane-wave like) will be converge into the central Zone 1; light signal with substantial wavefront distortions will result in intensity spots in Zone 2; highly randomized wavefront will result in intensity distribution in Zone 3.

Two different sectioned optical detector examples for the detector 107 are shown in FIGS. 3(c) and 3(d). In order to separate surface light from subsurface light, the optical detector 107 as shown in a first example in FIG. 3(c) is sectioned into and isolated 2 photo-sensing elements, i.e., a center disk sensor area 1 and a ring-shaped sensor area 2. These two photo-sensing elements are isolated electrically so that measured signals can be treated separately. The center disk sensor area 1 in FIG. 3(c) measures the returned probe light in Zone 1 and the ring-shaped sensor area 2 measures the combined light of the returned probe light in Zone 2 and 3.

In order to further differentiate light originated from different depths of the tissue, the photodetector may be sectioned into more than two elements as shown in a second example in FIG. 3(d): a center disk sensor area 1 and two concentric rings (middle ring sensor area 2 and outer ring sensor area 3). The center disk sensor area 1 senses mainly surface reflection and superficial scattering; the middle ring sensor area 2 detects subsurface light that carries substantial wavefront distortion; and the outer ring sensor area 3 preferentially detects light from deeper tissue volume with the most severe wavefront distortion.

The above examples in FIGS. 3(c) and 3(d) illustrate that the number of isolated optical sensing areas at different locations on or near the focal plane of the lens 105 can be increased so the number of different parts of the returned probe light from different depths that can be separately sensed and measured can be increased.

Figure 4:
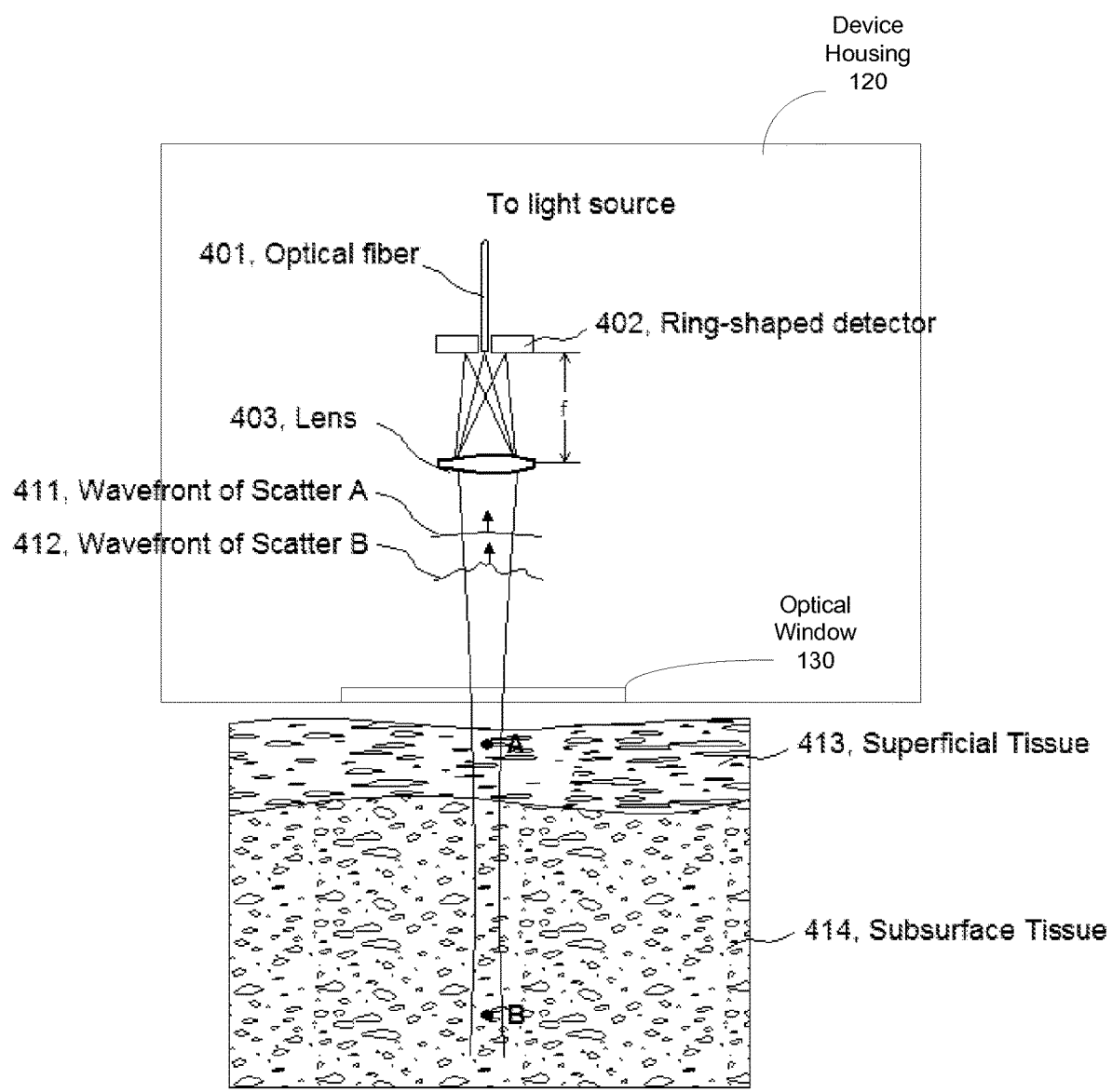
FIGS. 4-14 illustrated various examples of an non-invasive optical detection device based on optically discriminative detection

FIG. 4 shows an example of another non-invasive optical test device based on optically discriminative detection. A light source is coupled to an optical fiber 401 so that the probe light from the light source is routed in the optical fiber 401 to a lens assembly 403 that serves both as a collimator for directing collimated probe light towards the optical window 130 and a focusing lens for separating different portions of the returned probe light from the optical window 130 into different spatial portions for optically discriminative detection. As shown in FIG. 4, the tissue includes superficial tissue 413 and subsurface tissue 414. The structure A located in the near the skin surface in the superficial tissue 413 interacts with probe light to produce a wavefront 411 of the returned probe light and a structure B located in the subsurface tissue 414 interacts with the probe light to produce produces a wavefront 412 of the returned probe light. The photo-sensing element of the optical detector 402 is shaped as a hollow ring which excludes the central portion of the returned probe light (mostly from skin surface and shallow epidermis layers) from optical sensing and selects peripheral portion of the returned probe light (mostly from deep dermis layers) for optical sensing. The central void in the hollow ring also allows for the insertion of the optical fiber 401. This arrangement has the advantage of requiring little alignment of the photodetector 402 since its location and shape enable light from surface reflection and superficial scattering to be converged onto the fiber 401 itself without being sensed by the ring-shape photodetector 402. Consequently, the optical signal from the surface reflection and superficial scattering can be suppressed in the optical detection.

Figure 5:
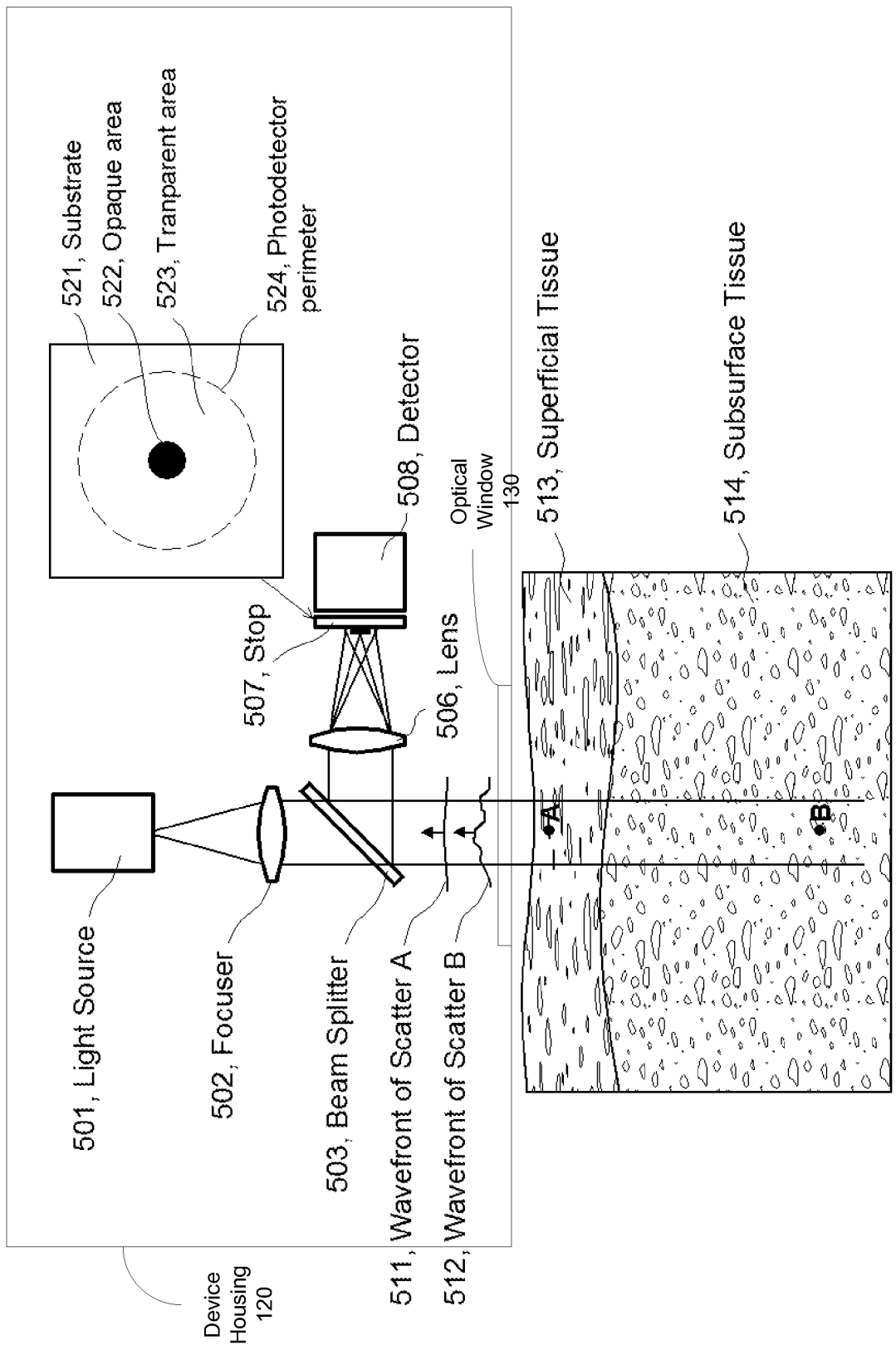

FIG. 5 shows another example of a non-invasive optical test device based on the optically discriminative detection in which a single element photo detector 508 is used in combination with a central beam stop 507 to preferentially receive returned probe light originated from subsurface volumes. In this example, the device includes a light source 501 that produces the probe light, a focuser 501 to focus the probe light, a beam splitter 503 to direct the probe light to the tissue and probe and to direct returned probe light from the tissue to the optical detection module. The tissue includes superficial tissue 513 and subsurface tissue 514. The structure A located in the near the skin surface in the superficial tissue 513 interacts with probe light to produce a wavefront 511 of the returned probe light and a structure B located in the subsurface tissue 514 interacts with the probe light to produce produces a wavefront 512 of the returned probe light. The lens 506 is placed in front of the photo detector 508 so that the detector 508 is at or near the focal plane of the lens 506. The beam stop 507 is placed at or near the focal plane of the lens 506 in front of the detector 508 to block surface reflection and superficial scattering from reaching the photodetector 508. The detector 508 includes a transparent area 523 with an outer detector perimeter 524. The beam stop 507 can be fabricated with an optical substrate, 521, on which an opaque center, 522, is formed, e.g., by using a thin-film deposition process. The diameter of the opaque center 522 should be set to obtain the desired blockage power. The larger the area is, the more exclusion power it has for distorted wavefront.

Figure 6:
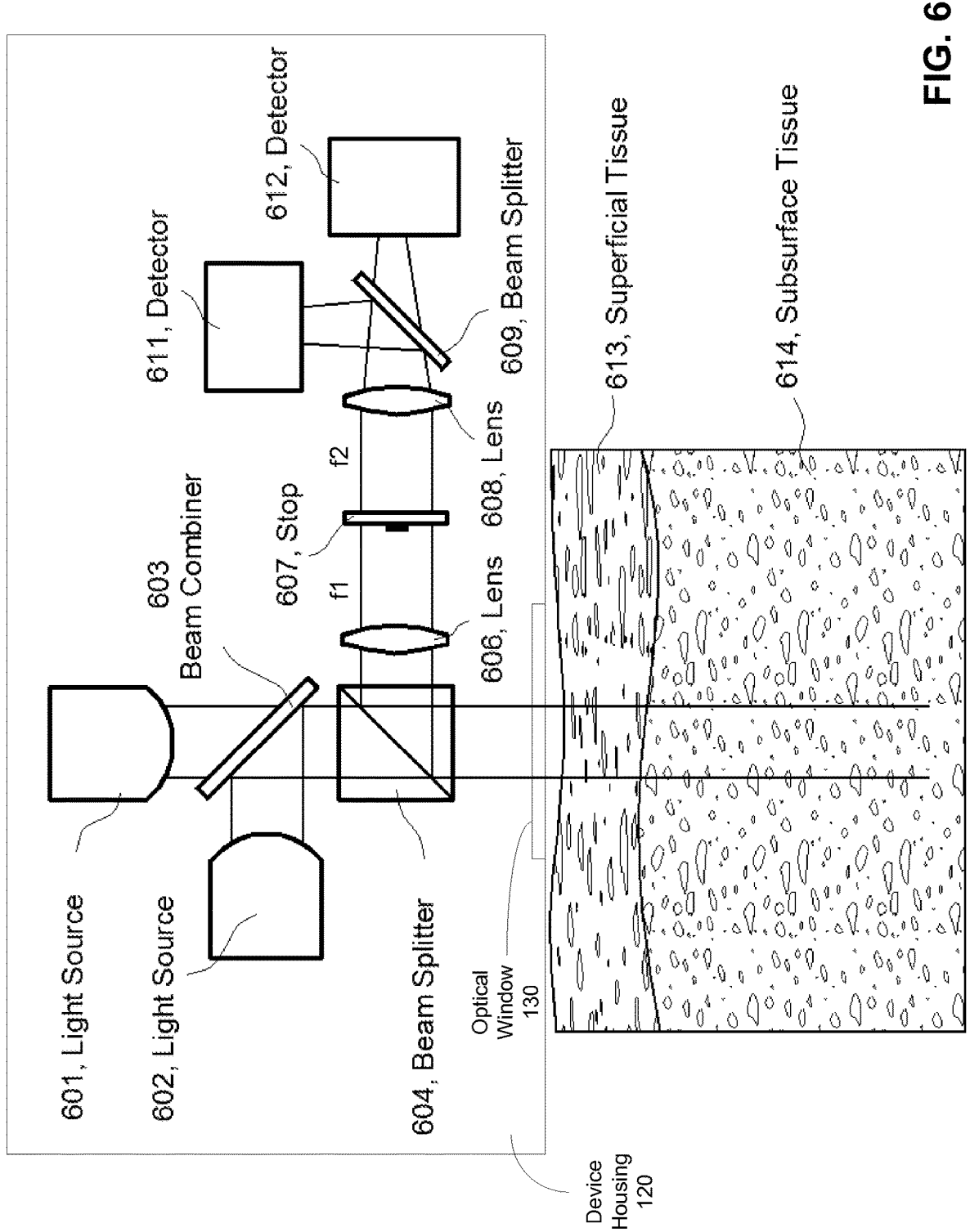

The use of the beam stop 522 is also suitable for other optical arrangements. FIG. 6 shows a design where two optical lenses 606 and 608 are separated from each other by a distance equal to the sum of the focal lengths of the two lenses 606 and 608 with focal lengths f1 and f2 which can be equal. This lens combination is used to direct the returned probe light to the optical detection unit. The light source can be a single light source or a combination of two or more light sources. As illustrated, different light sources emitting probe light at different wavelengths are used to produce the probe light (e.g., a beam combiner 603 for combining light beams from two light sources 601 and 602 at two different wavelengths). A beam splitter 604 is provided to direct the returned probe light from the optical window 130 to the two-lens system formed by lenses 606 and 608. The tissue includes superficial tissue 613 and subsurface tissue 614. A center beam stop 607 placed at the common focal plane between the two lenses 606 and 608 which blocks the central portion of the returned probe light and allows peripheral portion of the returned probe light to transmit through to the optical detection module. Lenses 606 and 608 placed on both sides of the beam stop 607 are used to direct the returned probe light to a beam splitter 609 that separates the light of the two different wavelengths into two different beams, each at a respective wavelength, to two optical detectors 611 and 612. The two photodetectors 611 and 612 are used to receive the collected light in the different wavelength bands, respectively. Comparisons of the two detected signals of the two photodetectors 611 and 612 can lead to more accurate determination of certain analyte that has a characteristic absorption at one wavelength. The second wavelength can be used for calibration.

The above use of two or more different probe light sources with different wavelengths or use probe light of a broad spectral range can be used to compare the absorption and scattering properties of tissue at different wavelengths. In some case a single light source, either a broadband light source such as a superluminescent light emitting diode (SLED) or tunable source such as a tunable laser, can cover the spectral range of interest. In other cases, it is more convenient to bring together light beams from multiple light sources, each covering a different wavelength band.

Figure 7:
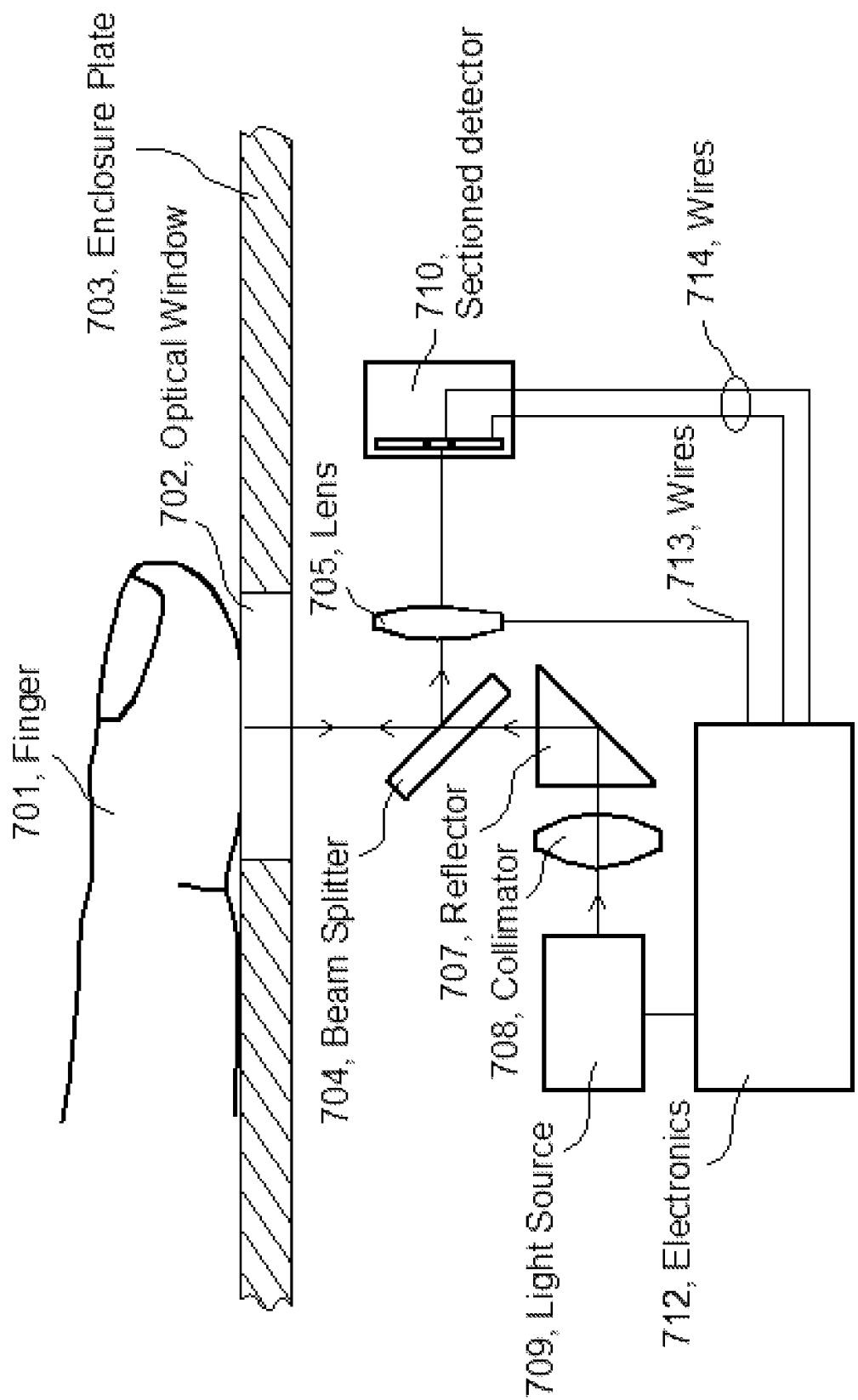

FIG. 7 shows an example of an optical test device for non-invasive measurements of blood analytes for measuring a finger 701. The device housing includes an enclosure plate 703 which is structured to include an optical window 703 like the optical window 130 in other examples for placing a finger thereon to perform the test. Light source 709, lens collimator 708, optical reflector 707 and optical beam splitter 704 are provided to route the probe light to the optical window 702. The returned probe light from the optical window 703 is directed by the beam splitter 704 to a lens assembly 705 and a sectioned photodetector 710 with different sensing elements to sense different portions of the returned probe light. For example, the sectioned photodetector 710 can include a central detector and a peripheral ring detector to acquire two light signals. The signal detected by the central detector corresponds to the surface reflection and superficial scattering; the optical signal sensed by the peripheral ring detector corresponds to light scattered by the subsurface tissue. Detector outputs 714 are directed to the device electronic unit 712 for processing and displaying to the user. It should be appreciated that detectors with more than two sensing elements can also be used in place of 710 for having more than two measured signals. The lens 705 can be actuated to change its position by a control signal via the signal line 713 to either scan the light onto the detector 710 or to adjust focus of the light onto the detector 710. To reduce the effects of signal variation due to light encountering different anatomy of the tissue, a beam scanner can be used.

Figure 8:
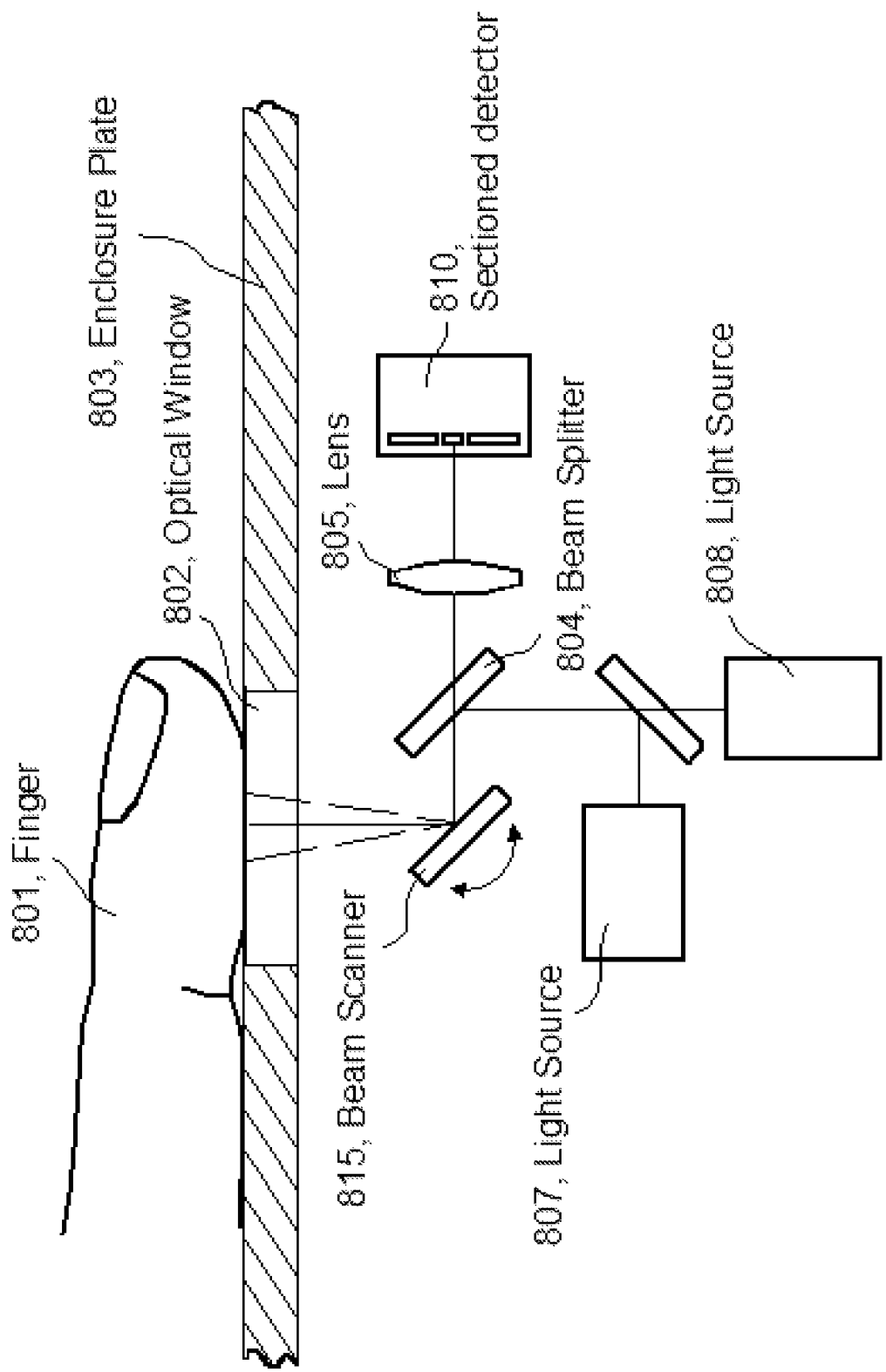

FIG. 8 shows another example where the probe light beam is scanned by a beam scanner, 815, to changing its position of impingement onto the finger 801 under test. An enclosure plate 803 has an optical window 802 on which the finger 801 is placed and illuminated by the probe light. A sectioned detector 810 is provided for the optical detection of the returned probe light and a lens 805 is placed in front the sectioned detector 810. This example also includes multiple light sources 807, 808 of different probe light wavelengths and a beam combiner 804 that combines such different probe beams into the final probe light to conducting the measurements.

Referring to FIG. 4 which shows an example of using the optical ring detector and a fiber to provide the optically discriminative detection, the design for the optically discriminative detection can be applied to combining multiple light sources of different probe wavelengths by providing a different optical fiber designated to each light source and using a beam combining device such as a beam combiner to combine light radiation from the different optical fibers coupled to different light sources respectively into a single probe beam for directing to the target tissue. The backscattered probe light from the target tissue at the different probe wavelengths can be separated into different returned probe light beams at the different probe wavelengths back to the respective optical fibers, respectively. The different optical ring detectors are then used to detect the different returned probe beams at the different probe wavelengths, respectively.

Figure 9:
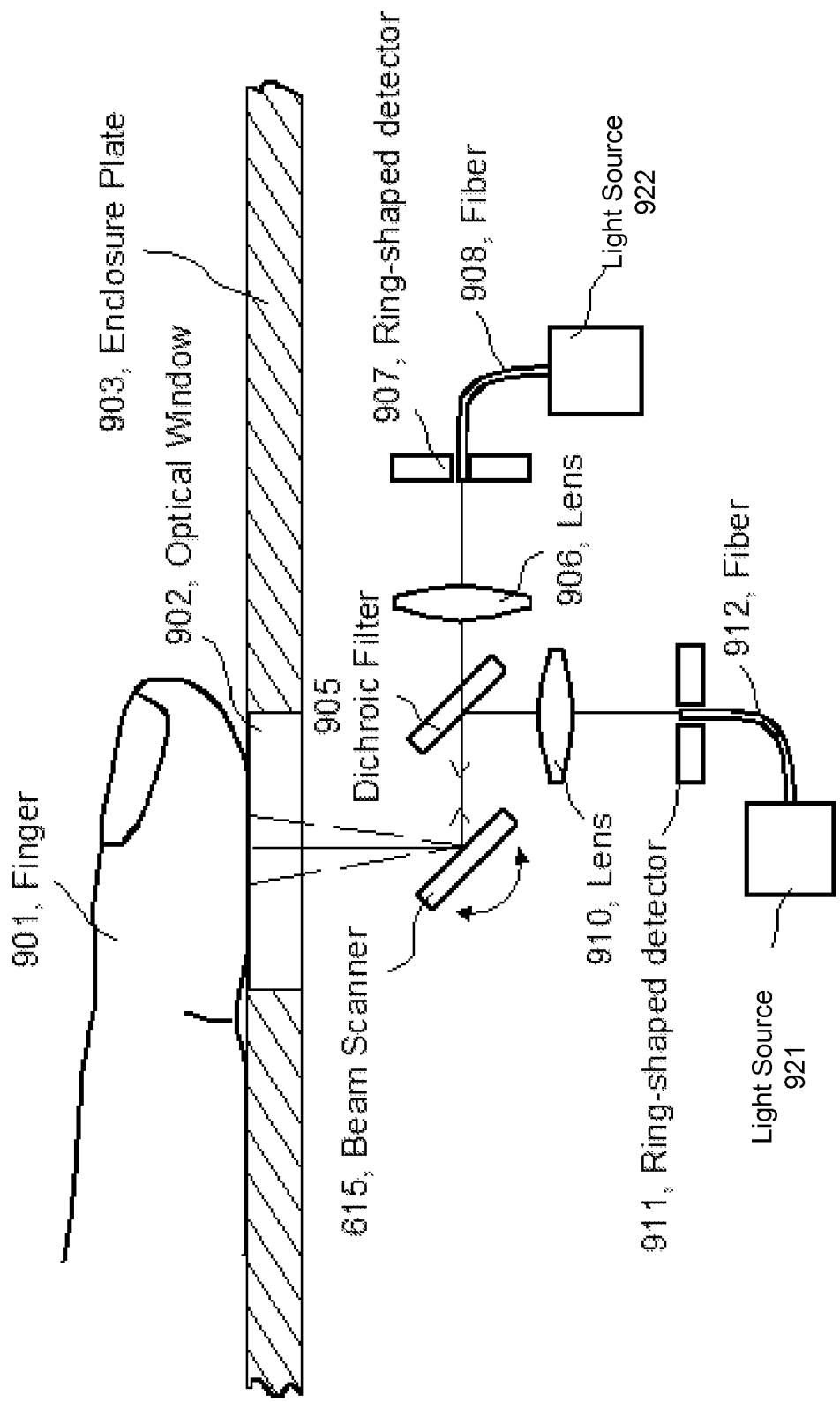

FIG. 9 shows an example of an optical test device that uses the optical ring detector design in FIG. 4 to combine two light sources 921 and 922 of different wavelengths. The device housing includes an enclosure plate 903 which is structured to include an optical window 903 like the optical window 130 in other examples for placing a finger 901 thereon to perform the test. Two fibers 912 and 908 are provided to guide the probe light from the two light sources 921 and 922 of different wavelengths, respectively. At terminal of each fiber, a ring shaped detector 907 or 911 is engaged to the fiber end similar to what is shown in FIG. 4 by inserting the fiber end into the center hole of the ring shaped detector so that the center portion of the returned probe light at a respective wavelength is not received by the ring shaped detector 907 or 911. A dichroic beam splitter or filter 905 is provided at the intersection of the two optical paths for the two probe light beams from the two light sources 921 and 922 to combine the light beams into a combined probe light beam for sensing at the optical window 902 in the device housing. The returned probe light at the two different wavelengths from the optical window 902 is directed back to the dichroic beam splitter or filter 905 to separate into two beams of the two different wavelengths that are respectively directed back to their respective paths with the two lenses 906 and 910. Each of the lenses 906 and 910 is, similar to the lens 403 in FIG. 4, used to perform both the collimation function when directing the probe light from the respective fiber to the dichroic beam splitter or filter 905 and the beam separating function when directing the returned probe light from the dichroic beam splitter or filter 905 to the respective ring shaped detector. The light sensing surfaces of the detectors 907 and 911 should be kept a focal length away from the respective lenses. A beam scanner may be used to scan the probe light onto the window 902 for measuring different locations of the finger 901.

Figure 10:
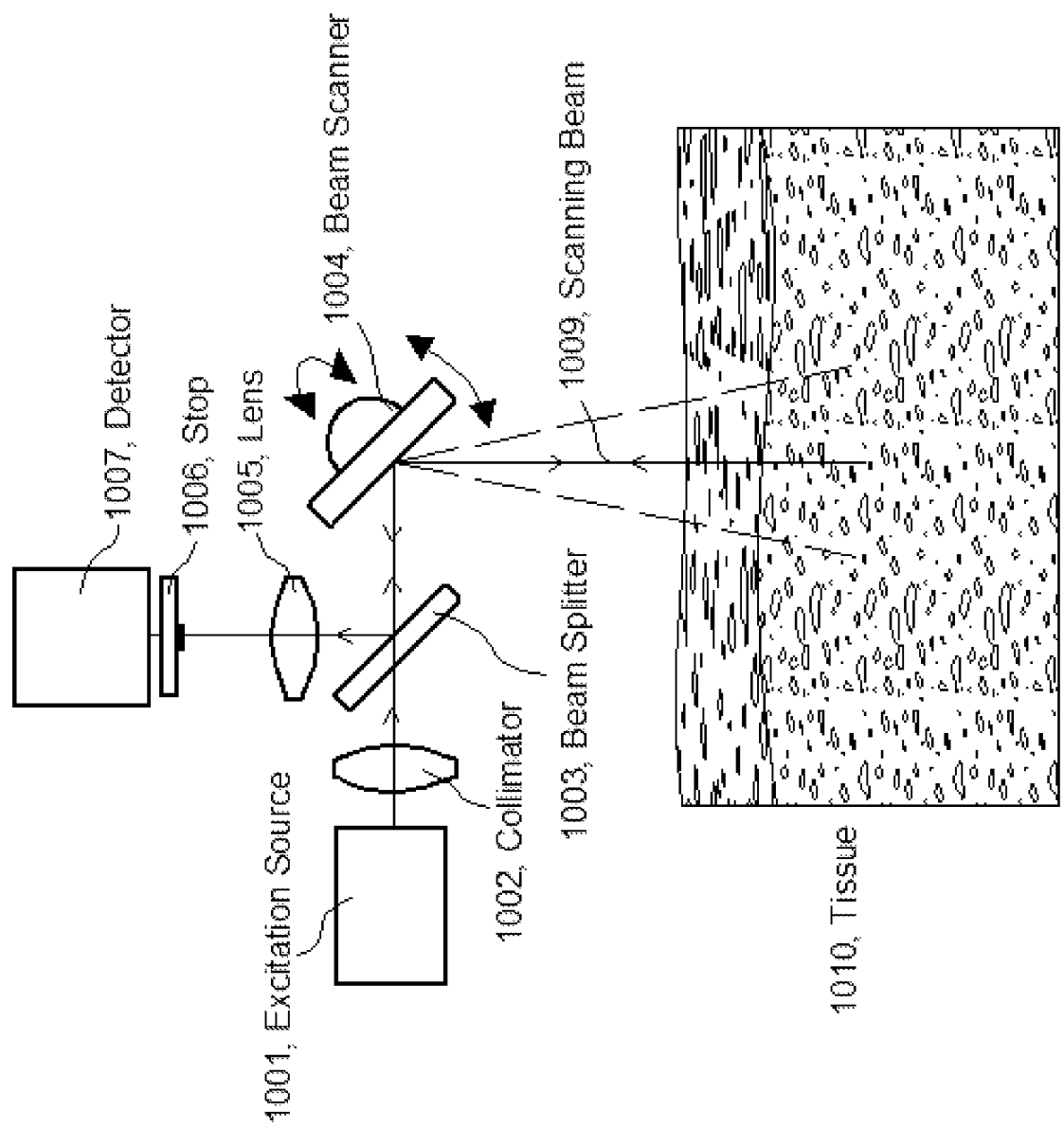
Figure 11:
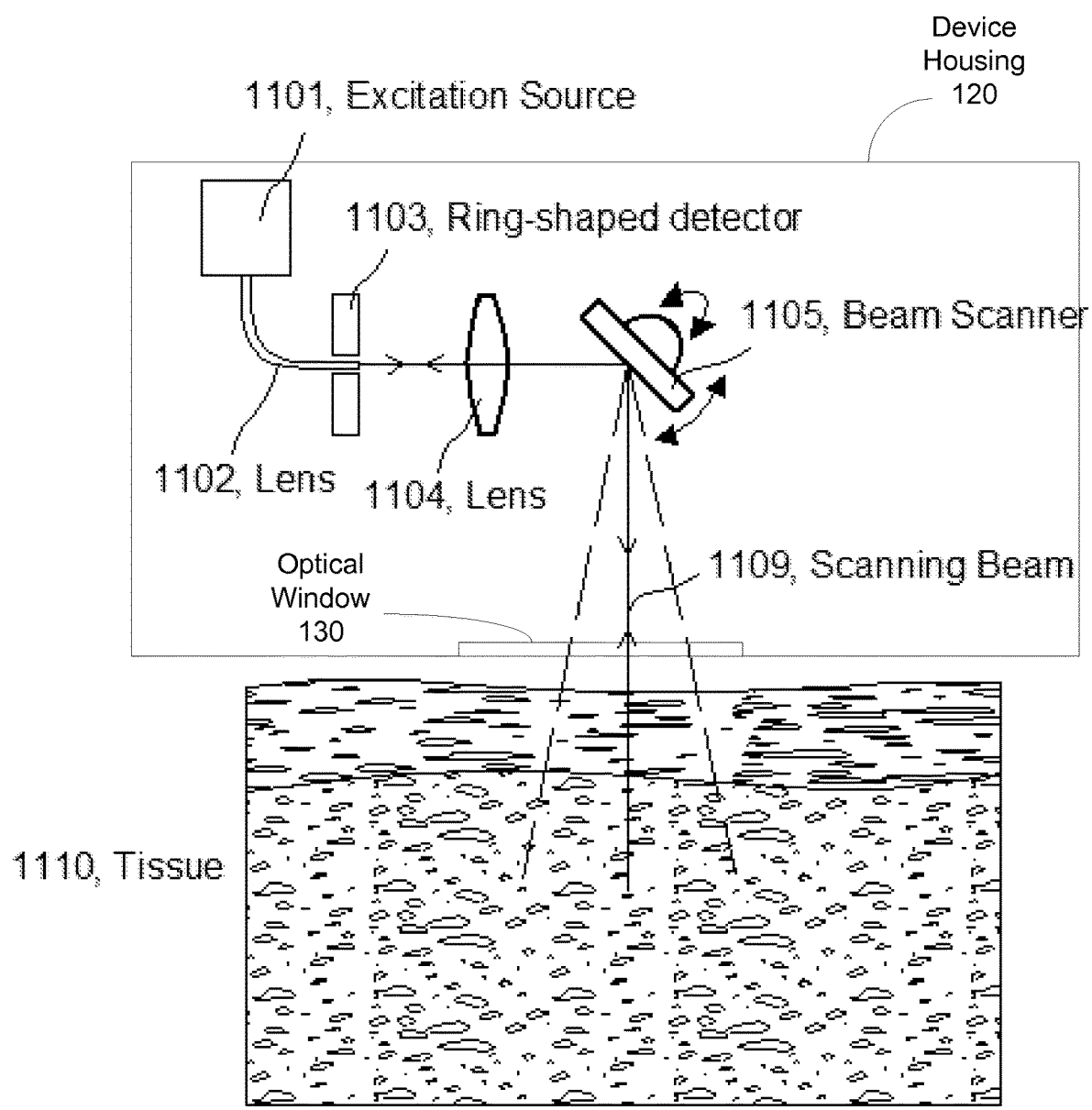
Figure 12:
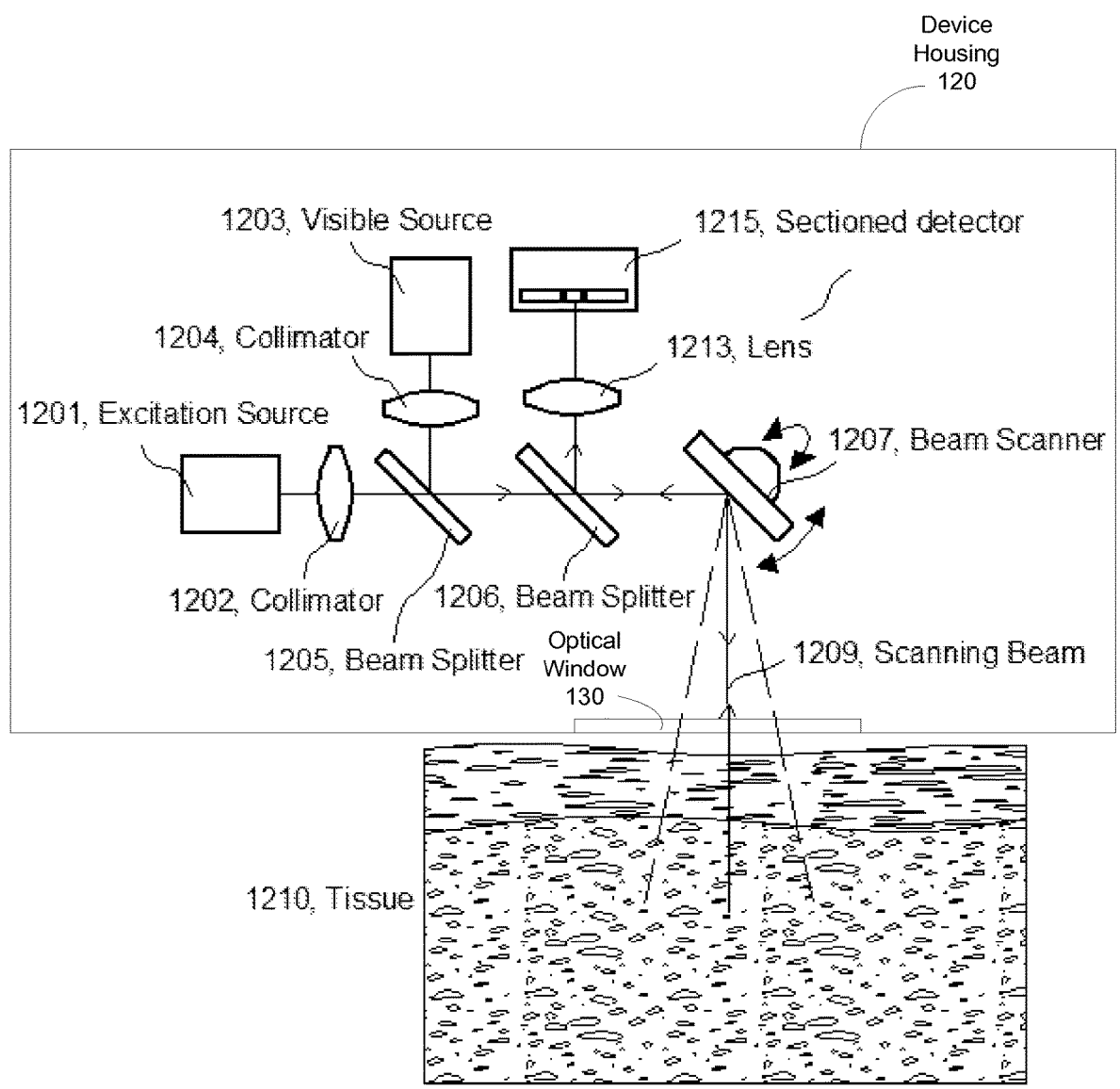

The optical method disclosed above can also be used for the differentiation of fluorescent light from different depths of a tissue. Shown in FIG. 10 is an optical arrangement that rejects fluorescent light from the superficial layer of the tissue with the use of a stop 1006 based on the examples in FIGS. 5 and 6. The optical detection is provided at the optical detector 1007. An excitation source 1001 is provided to produce probe light that passes through a collimator 1002 and a beam splitter 1003 to reach a beam scanner 1004 that scans the probe light as scanning beam 1009 to the tissue 1010 and directs the returned probe light towards the optical detector 1007. The stop 1006 prevents light with unperturbed wavefront, corresponding to light originated from the superficial layer, from reaching the photodetector. An alternative to the optical arrangement shown in FIG. 10 is the use of a ring detector with an inserted fiber for tissue excitation based on the design in FIG. 4, as shown in FIG. 11. FIG. 11 shows an example of a device including an excitation source 1101, a lens 1102, a ring-shaped detector 1103, a lens 1104, a beam scanner 1105 that scans the probe light through an optical windown 130 as the scanning beam 1109 to the tissue 1110, More functionalities can be included with the use of an optical arrangement as shown in another device example in FIG. 12 for measuring the tissue 1210. Two light sources are used: a visible light source 1203 and an excitation light source 1201 such as an IR light source. Two beam splitters 1205 and 1206 and two collimators 1202 and 1204 are provided as shown. A beam scanner 1207 is used to scan the probe light as the scanning beam 2019 to the tissue 1210 via the optical window 130. In this arrangement, a sectioned photodetector, 1215, is utilized so that fluorescence from the superficial tissue and subsurface tissue can be collected separately via lens 1213. The differentiation of the two signals can help in some diagnostic cases. The inclusion of the visible light source, 1203, is for highlighting tissue regions with certain diagnostically relevant characteristics. For instance, the two detected signals can be processed through a computing algorithm to yield a probability of having malignant cells in the area where light illuminates; the intensity of the visible light can be control to be proportional to the probability. This method of highlighting can be beneficial for direct visualization of diseased tissue areas.

Figure 13:
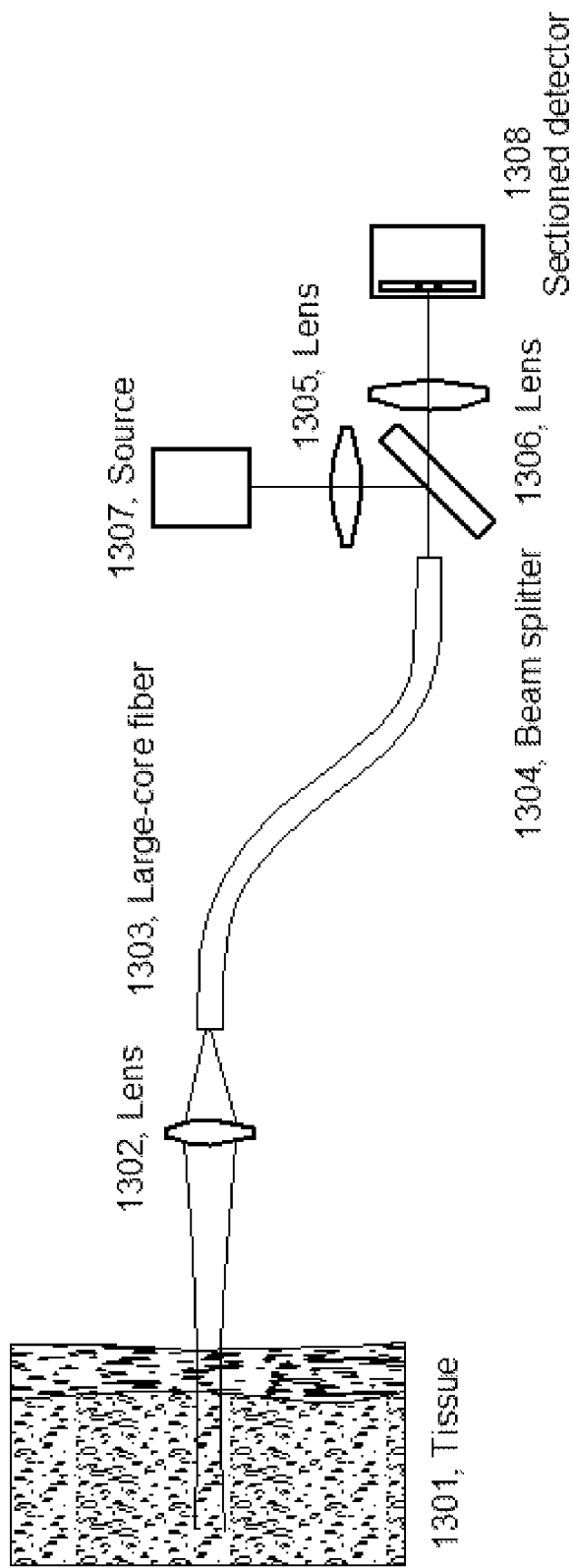

FIG. 13 shows an example of an optical test device that uses a large-core optical fiber, 1303, to collect returned probe light from the target issue and to transport the collected returned probe light signals from a vicinity of the tissue to a distant location of tissue 1301 via a lens 1302. A light source 1307 produces the probe light and a lens 1305 directs the probe light to a beam splitter 1304. The use of the large-core fiber 1303 can ensure that light signals with all wavefront characteristics are collected by the fiber 1303 due to its large cross section. Light signals with no or little wavefront disturbance will excite low-order propagation modes in the optical fiber 1303; light signals with highly distorted wavefronts will mainly excite high-order propagation modes in the fiber 1303. A sectioned photodetector, 1308, is utilized to receive light signals transported through the large-core fiber. The low-order propagation modes will be focused by the lens, 1306, to impinge on the center element of the detector; the high-order propagation modes will be focused to impinge on the ring element of the detector. This arrangement has the advantage of relocating some optical components away from the vicinity of the tissue so that a small probe can be constructed.

The present non-invasive optical test devices can be implemented in various configurations to meet specific needs or requirements of test applications. One of the advantages of the present non-invasive optical test devices is that, unlike various blood glucose testing kits on the market today, no blood or any biological sample is taken, and no biological or chemical processes are needed in performing the tests with the disclosed technology. In the present non-invasive optical test devices, the appropriate portion of the returned probe light can be selectively detected and analyzed automatically by the detection module built into the present non-invasive optical test devices without the need for operations or processing by the user or patient to produce the test results. In addition, the non-invasive nature of the optical testing is a highly desirable feature to eliminate any cutting and pain associated with various other blood testing devices or procedures. Furthermore, the present non-invasive optical test devices completely avoid errors associated with sample contamination that may occur in other blood testing devices or procedures. The combination of these and other features of the present non-invasive optical test devices renders the present non-invasive optical test devices suitable for clinical applications for improved testing efficiency and accuracy. Notably, the present non-invasive optical test devices can be configured to be particularly suitable for compact or portable configurations for clinical testing kits or self-testing kits used by patients.

Figure 14:
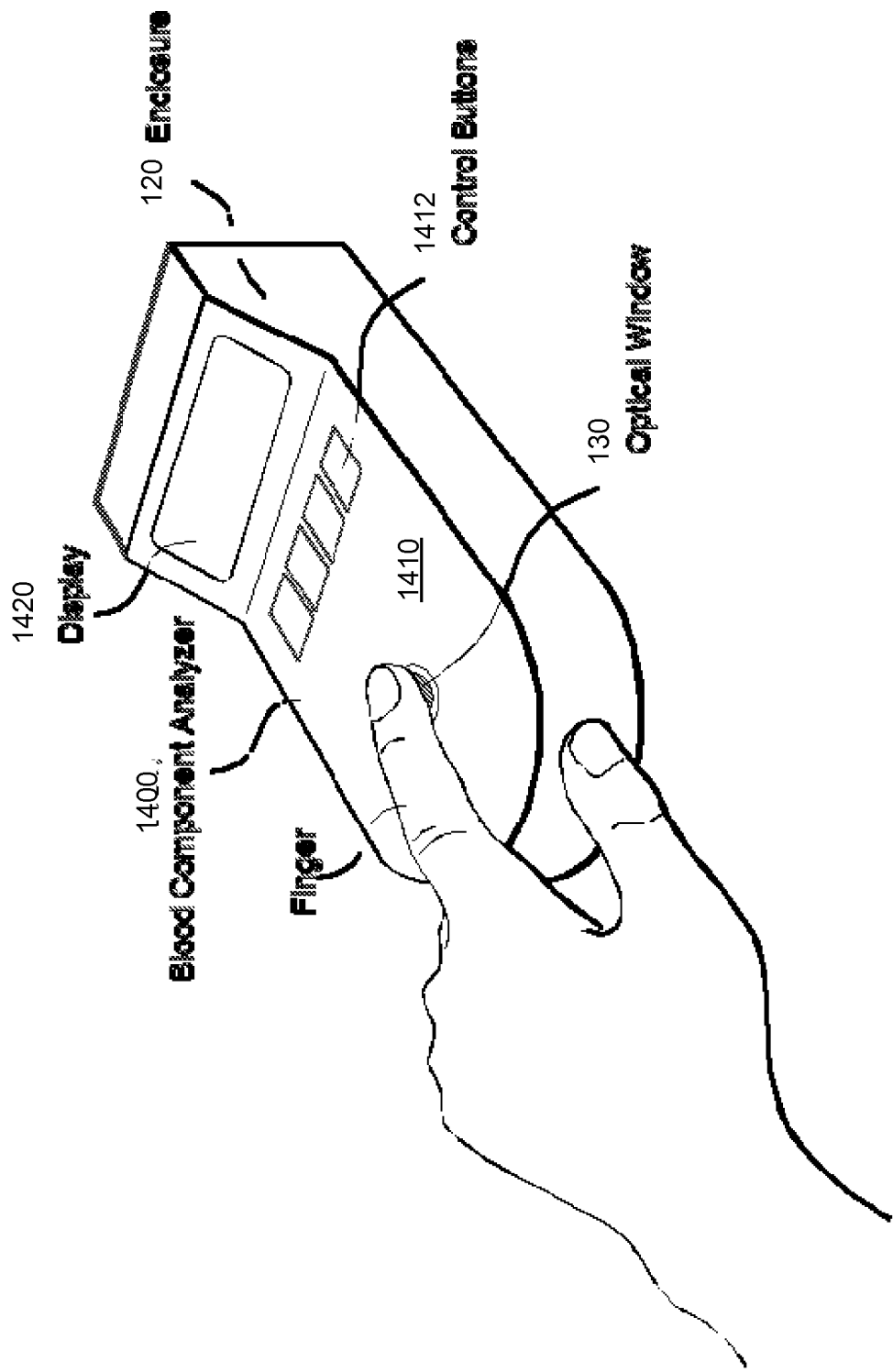

FIG. 14 shows an exterior of a compact or portable non-invasive optical test device 1400 based on the optically discriminative detection. This compact or portable device 1400 can be a blood component analyzer, a glucose test device based on measuring glucose-containing body fluids such as vasculature and interstitial fluids in the dermis layers, or other testing devices. Interior modules or components may be implemented by various examples or their combinations described in this document, e.g., FIGS. 1 and 4-12. The compact or portable device 1400 includes a device housing 120 with an enclosure and has a support panel or plate 1410 that supports the optical window 130 for placing a patient's finger or other body part thereon under test to receive the probe light coming out of the optical window 130 and to produce the returned probe light back into the optical window 130 for the optically discriminative detection. The support panel or plate 1410 also includes one or more control buttons 1412 for a patient or user to operate the device 1400 and a display screen 1420 for displaying the test results and other information. The control buttons 1412 may be used for various operations, e.g., turning on or off the power of the device, activating or deactivating the optical detection, or selecting control display modes of the test results and other device status information on the display screen. The control buttons 1412 may be physical buttons, soft key buttons or a combination of both physical buttons and soft key buttons. Both the control buttons 1412 and the display screen 1420 are coupled to the device control unit inside the device housing 120, e.g., the device control unit 140 in FIG. 1 which includes electronics and a processor and operates to provide user interface and control functions for the user to operate the device when performing the test and to provide a user display feature to output the test results and other user control functions. In some implementations, the display screen 1420 can be a touch screen that provides both the display window for displaying information and a touch interface for user control operations that may replace part of or the entirety of the control buttons 1412.

In implementing the present non-invasive optical test devices based on optically discriminative detection, the wavelengths or spectral range of the probe light can be selected based on the types of the target tissues or objects to be detected. Different applications tend to use different probe wavelengths. In various medical tests, for example, probe light in the visible wavelengths (roughly from 400 nm to 800 nm), near infrared (roughly from 900 nm to 2.5 microns) or short wavelength wavelengths have been used due to various factors, e.g., availability of the light sources and detectors, penetration depths of such light in tissues. Other optical spectral ranges for the probe light, such as the mid infrared spectral range roughly from 3 microns to 8 microns and long-wavelength infrared spectral range roughly from 8 microns to 30 microns, may be used for the probe light in implementing present non-invasive optical test devices based on optically discriminative detection. As a specific example, glucose is known to exhibit unique sets of optical absorption peaks in the spectral range roughly from 8 microns to 11 microns. See, for example, von Lilienfeld-Toal et al. in "A novel approach to non-invasive glucose measurement by mid-infrared spectroscopy: The combination of quantum cascade lasers (QCL) and photoacoustic detection with sufficient specificity and reliability" published in Vibrational Spectroscopy, Vol. 28, pages 209-215, 2005. Therefore, the present non-invasive optical test devices based on optically discriminative detection can be designed and adopted (e.g., in the portable configuration in FIG. 14) to conduct non-invasive glucose tests without taking blood samples. The light source for the probe light can be in the spectral range from 8 microns to 11 microns. In this and other applications based on the mid infrared (MIR) spectral range and long-wavelength infrared (LWIR) spectral range, one technical issue is the limited penetration depth of such light into the tissues due to strong water absorption and other factors. The optically discriminative detection described above can be used to improve the detection sensitivity of returned probe light from deeper tissues and therefore can be combined with the use of probe light in the mid infrared (MIR) spectral range and long-wavelength infrared (LWIR) spectral range to provide useful detection devices for non-invasive glucose testing and a range of other applications.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is what is described and illustrated, including:

1. A non-invasive optical device for optically characterizing a target tissue under the skin, comprising:
a device housing that forms an enclosure and an optical window in the enclosure that transmits light and provides a surface for a person to place a finger or body part thereon;
a light source located inside the device housing to produce probe light that transmits through the optical window to reach the finger or body part and to produce returned probe light from the finger or body part which carries information of an illuminated part of the finger or the body part for optically characterizing a target tissue inside the finger or body part;
a lens located inside the device housing in an optical path of the returned probe light to perform a Fourier transform on different portions of the returned probe light of different optical wave vectors to direct the different portions of the returned probe light onto different locations on or near a focal plane of the lens;
an optical detector module located inside the device housing and positioned in a detector plane that is at or near the focal plane of the lens and configured to include one or more optical detectors positioned at different positions in the detector plane from an optical axis of the lens to spatially selective one or more selected portions of the returned probe light from the different portions of the returned probe light for detecting the target issue while spatially rejecting, from the one or more optical detectors, other portions of the different portions of the returned probe light that represent majority of the probe light returned by the skin surface and tissue layers above the target tissue; and
a processing unit that receives output of the optical detector and processes the received output to extract information of the target tissue based on a relationship between positioning of the one or more optical detectors in the detector plane and depths of the different portions of the returned probe light generated below the skin surface including the target tissue.

2. The device as in claim 1, wherein:
the optical detector module is located on the focal plane of the lens.

3. The device as in claim 1, wherein:
the optical detector module includes, in addition to the one or more optical detectors that receive the selective one or more selected portions of the returned probe light, at least another optical detector that is located to receive the other portions of the different portions of the returned probe light that are not received by the one or more optical detectors.

4. The device as in claim 3, wherein:
the one or more optical detectors of the optical detector module are located off an optical axis of the lens to detect portions of the returned probe light with large angles relative to the optical axis and the at least another optical detector is located on or near the optical axis of the lens to detector the other portions of the returned probe light with small angles relative to the optical axis.

5. The device as in claim 1, wherein:
the optical detector module includes (1) a ring shaped optical detector that receives as part of the one or more optical detectors to receive the one or more selected portions of the returned probe light for detecting the target issue, and (2) a center disk optical detector located within and isolated from the ring shaped optical detector to receive the other portions of the different portions of the returned probe light that represent majority of the probe light returned by the skin surface and tissue layers above the target tissue.

6. The device as in claim 1, wherein:
the optical detector module includes multiple different optical detectors that are isolated from one another and located at different locations on or near the focal plane of the lens to, respectively, receive different portions of the returned probe light from, respectively, different regions with different depths between the skin surface and the target tissue.

7. The device as in claim 1, comprising:
a beam scanner in the device housing that scans the probe light onto the optical window.

8. The device as in claim 1, comprising:
an optical fiber including a first fiber terminal coupled to receive the probe light from the light source and a second terminal coupled to output the probe light to be directed to the optical window;
wherein the optical detector module includes a ring shaped optical detector structured to include central hole in which the second terminal of the optical fiber is inserted to collected a central portion of the returned probe light, and
wherein the lens is located in an optical path between the second terminal of the optical fiber and the optical window to be away from the ring shaped optical detector so that the ring shaped optical detector is at or near the focal plane of the lens and to receive peripheral portions of the returned probe light.

9. The device as in claim 1, wherein:

the optical detector module includes an optical detector for receiving the returned probe light;

the device further includes a beam stop formed of an optically opaque material and located at or near a center of the optical detector to block a center portion of the returned probe light from reaching the optical detector.

10. The device as in claim 1, wherein:

the light source produces the probe light in a range of different wavelengths.

11. The device as in claim 10, wherein:

the range of different wavelengths is from 8 microns to 11 microns in which glucose exhibits signature optical absorption peaks.

12. The device as in claim 1, wherein:

the light source includes different light sources that emit light at different wavelengths, respectively; and the device includes a beam combiner that combines the light of different wavelengths as the probe light to be directed to the optical window.

13. The device as in claim 12, wherein:

the different wavelengths are between 8 microns and 11 microns in which glucose exhibits signature optical absorption peaks.

14. A non-invasive optical device for optically characterizing a target tissue under the skin, comprising:

a device housing that forms an enclosure and an optical window in the enclosure that transmits light and provides a surface for a person to place a finger or body part thereon;

a light source located inside the device housing to produce probe light that transmits through the optical window to reach the finger or body part and to produce returned probe light from the finger or body part which carries information of an illuminated part of the finger or the body part for optically characterizing a target tissue inside the finger or body part;

a lens located inside the device housing in an optical path of the returned probe light to perform a Fourier transform on different portions of the returned probe light of different optical wave vectors to direct the different portions of the returned probe light onto different locations on or near a focal plane of the lens;

an optical detector module located inside the device housing and positioned at or near the focal plane of the lens and configured to include one or more optical detectors to spatially selective one or more selected portions of the returned probe light from the different portions of the returned probe light for detecting the target issue while spatially rejecting, from the one or more optical detectors, other portions of the different portions of the returned probe light that represent majority of the probe light returned by the skin surface and tissue layers above the target tissue; and a processing unit that receives output of the optical detector and processes the received output to extract information of the target tissue, wherein:

the optical detector module includes (1) a first ring shaped optical detector that receives one of the one or more optical detectors to receive the one or more selected portions of the returned probe light for detecting the target issue, (2) a second ring shaped optical detector located inside and isolated from the first ring shaped optical detector to receive portions of the returned probe light that represent majority of the returned probe light returned by a middle region between the skin surface and the target tissue, and (3) a center disk optical detector located within and isolated from the first and second ring shaped optical detectors to receive the other portions of the different portions of the returned probe light that represent majority of the probe light returned by the skin surface and tissue layers above the middle region and the target tissue.

15. The device as in claim 14, comprising:

a beam scanner in the device housing that scans the probe light onto the optical window.

16. The device as in claim 14, comprising:

an optical fiber including a first fiber terminal coupled to receive the probe light from the light source and a second terminal coupled to output the probe light to be directed to the optical window, wherein the lens is located in an optical path between the second terminal of the optical fiber and the optical window.

17. The device as in claim 14, comprising:

a beam stop formed of an optically opaque material and located at or near a center of the optical detector to block a center portion of the returned probe light from reaching the optical detector.

18. The device as in claim 14, wherein:

the light source produces the probe light in a range of different wavelengths.

19. The device as in claim 18, wherein the range of different wavelengths is from 8 microns to 11 microns in which glucose exhibits signature optical absorption peaks.

20. The device as in claim 14, wherein:

the light source includes different light sources that emit light at different wavelengths, respectively; and the device includes a beam combiner that combines the light of different wavelengths as the probe light to be directed to the optical window.

21. The device as in claim 20, wherein:

the different wavelengths are between 8 microns and 11 microns in which glucose exhibits signature optical absorption peaks.

* * * * *